United States Patent
Zhang et al.

(10) Patent No.: US 10,444,222 B2
(45) Date of Patent: Oct. 15, 2019

(54) HEMOLYSIS DETECTION USING INTRACELLULAR ANALYTE CONCENTRATIONS

(71) Applicant: Siemens Healthcare Diagnostics Inc., Tarryrtown, NY (US)

(72) Inventors: Wei Zhang, Needham, MA (US); Kevin Horan, Raynham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 153 days.

(21) Appl. No.: 15/535,944

(22) PCT Filed: Dec. 18, 2015

(86) PCT No.: PCT/US2015/066691
§ 371 (c)(1),
(2) Date: Jun. 14, 2017

(87) PCT Pub. No.: WO2016/100824
PCT Pub. Date: Jun. 23, 2016

(65) Prior Publication Data
US 2017/0370904 A1 Dec. 28, 2017

Related U.S. Application Data

(60) Provisional application No. 62/094,455, filed on Dec. 19, 2014.

(51) Int. Cl.
| | | |
|---|---|---|
| G01N 33/49 | (2006.01) | |
| G01N 27/327 | (2006.01) | |
| G01N 27/49 | (2006.01) | |
| G01N 33/48 | (2006.01) | |
| C12Q 1/00 | (2006.01) | |

(52) U.S. Cl.
CPC ......... *G01N 33/492* (2013.01); *G01N 27/327* (2013.01); *G01N 27/49* (2013.01); *G01N 33/48* (2013.01); *G01N 33/4915* (2013.01); *C12Q 1/005* (2013.01)

(58) Field of Classification Search
CPC ...... G01N 33/492; G01N 33/48; G01N 27/49; G01N 27/327; G01N 33/4915; C12Q 1/005
See application file for complete search history.

(56) References Cited

U.S. PATENT DOCUMENTS

| | | |
|---|---|---|
| 5,416,026 A | 5/1995 | Davis |
| 5,460,972 A | 10/1995 | Altura et al. |
| 8,548,772 B2 | 10/2013 | Brouwer et al. |

(Continued)

FOREIGN PATENT DOCUMENTS

WO 2014025961 A1 2/2014

OTHER PUBLICATIONS

European Search and Written Opinion of European Application No. 15871170.5 dated Nov. 17, 2017.

(Continued)

*Primary Examiner* — Lore R Jarrett
(74) *Attorney, Agent, or Firm* — Dunlap Codding P.C.

(57) ABSTRACT

This disclosure relates to the detection of whole blood hemolysis in a sample of whole blood. More specifically, this disclosure describes detecting hemolysis using one or more novel ratios of intercellular concentrations of whole blood analytes.

12 Claims, 4 Drawing Sheets

(56) References Cited

U.S. PATENT DOCUMENTS

2008/0128606 A1* 6/2008 Grant .................. G01N 33/743
250/282
2011/0318767 A1* 12/2011 Takagi .................. C12Q 1/006
435/14
2014/0262831 A1 9/2014 Balasubramanian et al.

OTHER PUBLICATIONS

International Search Report and Written Opinion of International Application No. PCT/US2015/066691 dated Feb. 26, 2016.
Lüdi et al., "Some Properties of a System for Sodium-Dependent Outward Movement of Magnesium From Metabolizing Human Red Blood Cells", 1987, J Physiol., vol. 390, pp. 367-382.
Yalcinkaya et al., "A Portable Battery-Operated Multi-Sensor-Array for Whole Human Blood Analysis", 1997, Proceedings of the 19th Annual International Conference of the IEEE Engineering in Medicine and Biology Society, pp. 2350-2353.
Dimeski et al., "Ion Selective Electrodes (ISEs) and interferences—A review", 2009, Elsevier—Clinica Chimica Acta, pp. 1-9.

\* cited by examiner

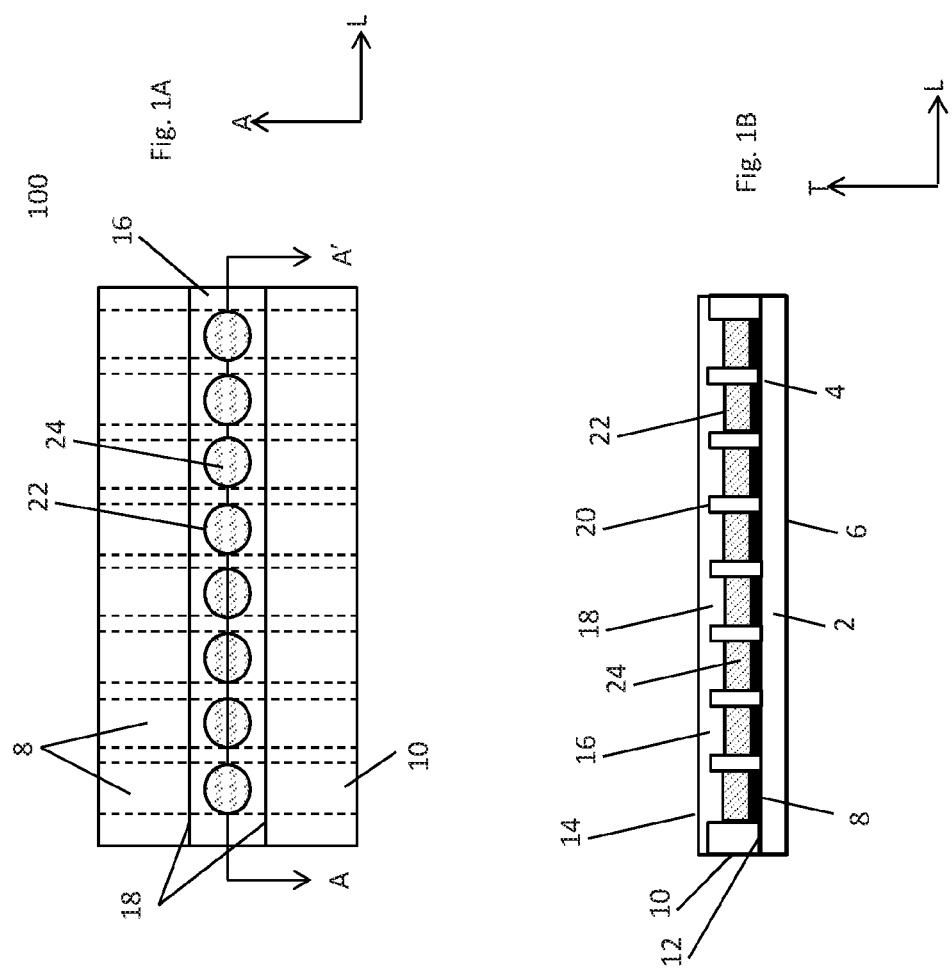

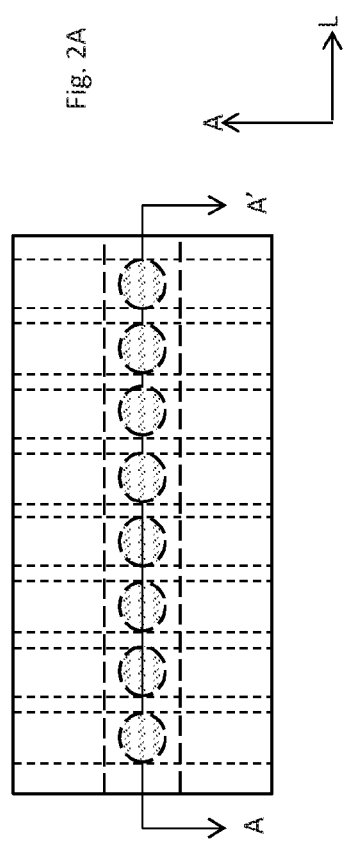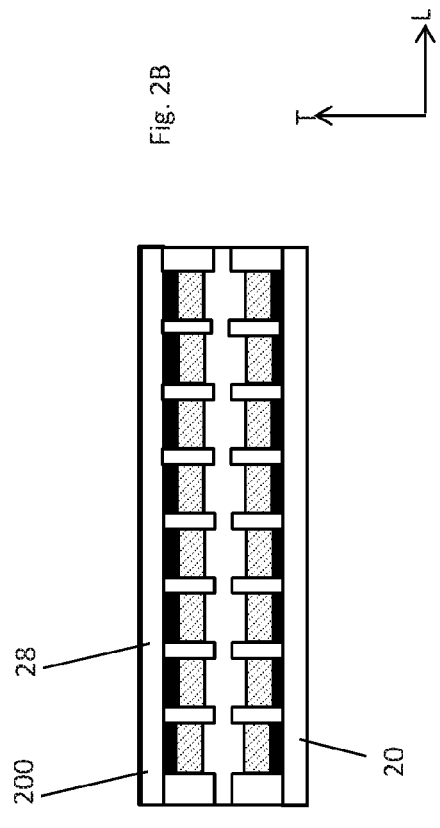

HEMOLYSIS DETECTION USING INTRACELLULAR ANALYTE CONCENTRATIONS

The subject application claims benefit under 35 USC § 119(e) of U.S. Provisional Application No. 62/094,455, filed Dec. 19, 2014. The entire contents of the above-referenced patent application are hereby expressly incorporated herein by reference.

BACKGROUND

1. Field of the Disclosure

This disclosure relates to the detection of whole blood hemolysis in a sample of whole blood. More specifically, this disclosure describes detecting hemolysis using one or more intercellular concentrations of whole blood analytes.

2. Brief Description of the Related Art

Hemolysis refers to the destruction or dissolution of red blood cells (RBCs) which results in the release of intracellular elements—such as potassium ions ($K^+$), magnesium ions ($M^{++}$), sodium ions ($Na^+$) and calcium ions ($Ca^{++}$) into the surrounding plasma. The occurrence of hemolyzed RBCs may be the result of a patient's medical condition or by the mishandling the sample itself. When severe enough, hemolysis may result in inaccurate laboratory test results. For example, in blood gas and electrolyte testing it is known that—depending on the severity—hemolysis will cause an increase in the sample potassium level. In addition, it is known that cardiac specific isoforms of troponin (cTnT) levels are decreased in samples with hemolysis and cardiac muscle tissue (cTnI) levels have been shown to be increased in samples with hemolysis.

Detecting the extent of hemolysis in whole blood samples has been traditionally difficult. Prior art tests involve filtering or centrifuging the whole blood—which generates plasma that is interrogated optically either in the near-infrared (NIR) or visible wavelength regions. However, these testing techniques require specialized equipment, and are often complex—thereby making them ineffective for point of care applications.

SUMMARY OF THE INVENTIVE CONCEPT(S)

In one aspect, the inventive concepts disclosed herein are directed to a system for, and method of, determining a level of hemolysis of a sample of whole blood. The method being comprised of, for example: receiving a first intercellular concentration of a first compound in the whole blood sample, the first intercellular concentration having been obtained from a first sensor disposed on a sensor cartridge, the first sensor being specific to the first compound, an intracellular concentration of the first compound being higher than the intercellular concentration in the whole blood sample; receiving a second intercellular concentration of a second compound in the whole blood sample, the second concentration having been obtained from a second sensor on the sensor cartridge that is specific to the second compound, an intracellular concentration of the second compound being higher than the intercellular in the whole blood sample; receiving a third intercellular concentration of a third analyte, the third concentration having been obtained from a third sensor on the sensor cartridge that is specific to the third compound, the third analyte being a compound with an intracellular concentration lower than the intercellular concentration in the whole blood sample; computing a first ratio of the first concentration to the third concentration; computing a second ratio of the second concentration to the third concentration, and determining the degree of hemolyzation of the whole blood sample based on the first ratio and the second ratio; and outputting the determination to a medical professional.

In another aspect, the inventive concepts disclosed herein are directed to a system comprising at least one processor and a non-transitory computer-readable medium that stores instructions that, when executed by the at least on processor cause the system to determine a level of hemolysis of a sample of whole blood, by: administering whole blood to a sensor cartridge containing at least a K, Mg, Ca, and lactate sensor; determining a first intercellular concentration of a first compound in the whole blood sample, the first concentration having been obtained from a first sensor disposed on a sensor cartridge, the first sensor being specific to the first compound, an intracellular concentration of the first compound being higher than the intercellular concentration in the whole blood sample; determining a second intercellular concentration of a second compound in the whole blood sample, the second concentration having been obtained from a second sensor on the sensor cartridge that is specific to the second compound, an intracellular concentration of the second compound being higher than the intercellular in the whole blood sample; determining a third intercellular concentration of a third analyte, the third concentration having been obtained from a third sensor on the sensor cartridge that is specific to the third compound, the third analyte being a compound with an intracellular concentration lower than the intercellular concentration in the whole blood sample; computing a first ratio of the first concentration to the third concentration; computing a second ratio of the second concentration to the third concentration; determining the degree of hemolyzation of the whole blood sample based on the first ratio and the second ratio; and outputting the determination to a medical professional.

BRIEF DESCRIPTIONS OF THE DRAWINGS

FIGS. 1A and 1B depict, respectively, a top view and a side view along line A-A' of an illustrative sensor array;

FIGS. 2A and 2B depict, respectively, a top view and a side view along line A-A' of another illustrative sensor array;

DETAILED DESCRIPTION OF THE INVENTIVE CONCEPT(S)

Figure 3:
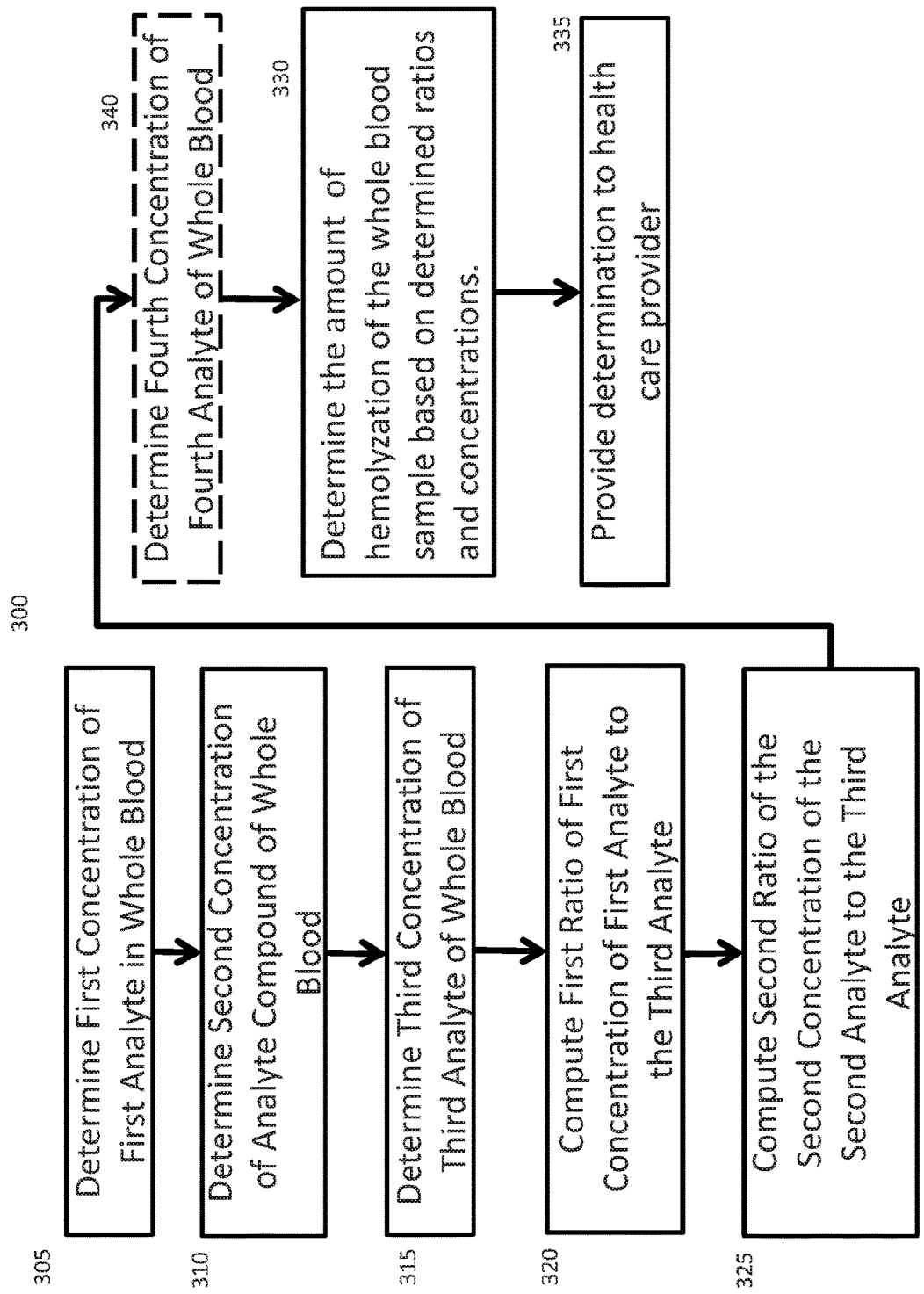
FIG. 3 depicts an exemplary method of determining the degree of hemolysis in a sample.

Before explaining at least one embodiment of the inventive concepts disclosed herein in detail, it is to be understood that the inventive concepts are not limited in their application to the details of construction and the arrangement of the components or steps or methodologies set forth in the following description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way.

In the following detailed description of embodiments of the inventive concepts, numerous specific details are set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example. As one example, "about" may refer a value that is ±10% of the stated value.

As used herein, the term "sample" and variations thereof is intended to include biological tissues, biological fluids, chemical fluids, chemical substances, suspensions, solutions, slurries, mixtures, agglomerations, tinctures, slides, powders, or other preparations of biological tissues or fluids, synthetic analogs to biological tissues or fluids, bacterial cells (prokaryotic or eukaryotic), viruses, single-celled organisms, lysed biological cells, fixed biological cells, fixed biological tissues, cell cultures, tissue cultures, genetically engineered cells and tissues, genetically engineered organisms, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The embodiments of the sensing array disclosed herein may be understood with reference to a first, second, and third direction such as, for example, lateral direction 'A', a longitudinal direction 'L'; which is perpendicular to lateral direction 'A', and a transverse direction 'T' which is perpendicular to longitudinal direction 'L.' The longitudinal direction L and the lateral direction A extend horizontally as illustrated, and the transverse direction T extends vertically, though it should be appreciated that these directions may change depending, for instance, on the orientation of the sensor array. It should also be understood that first direction may be referred to as the lateral direction. It should also be understood that second direction may be referred to as the longitudinal direction. It should also be understood that third direction may be referred to as the transverse direction.

The inventive concepts disclosed herein are generally directed to a device and technique for determining the severity of hemolysis in a patient's sample of whole blood using the intracellular vs. intercellular levels of certain analytes within a sample of whole blood. By utilizing the corresponding analyte sensors—which are widely used—a sensor array can be constructed that does not need a dedicated hemolysis sensor. This allows for the use of a sensor array—that can be devoid of a dedicated hemolysis detector—to detect the extent of hemolysis using a combination of analyte concentrations obtained by widely used analyte sensors.

FIGS. 1A and 1B depict, respectively, a top view and a side view along line A-A' of illustrative sensor array 100. Sensor array 100 includes a planar substrate 2. Planar substrate 2 may be substantially planar with a substantially planar upper surface 4 and substantially planar lower surface 6. The upper surface 4 and lower surface 6 both extend in the lateral direction A and the longitudinal direction L and are separated by a thickness extending along the transverse direction T. Planar substrate 2 may be formed using a variety of methods and materials known to a person of ordinary skill in the art. For example, planar substrate may be constructed using one or more of, for example, ceramic, polymer, foil, flex PCB, PET, PI, etc.

Sensor array 100 further includes one or more of: (1) a conductive layers, comprised of coplanar conductors 8, disposed on—and coplanar with—upper surface 4 of the planar substrate 2 (eight examples of conductors 8 are depicted in FIGS. 1A and 1B); and (2) a planar dielectric layer 10 disposed adjacent to as well as coplanar with the upper surface 4 of the substrate and planar conductors 8—the planar conducts 8 being disposed in between planar dielectric layer 10 and the planar substrate 2.

While not shown in the Figures, the conductors 8 are electrically coupled to a contact region elsewhere on the sensor assembly 100. These electrical contacts enable the sensor assembly 100 to be electrically connected to a processor and/or an external device (as is described further below).

Coplanar conductors 8 may be formed using a variety of methods and materials known to a person of ordinary skill in the art. For example, coplanar conductors 8 may be formed using a thick film approach (e.g., screen printing, rotogravure, pad printing, stenciling conductive material such as carbon, Cu, Pt, Pd, Au, and/or Nanotubes, etc. . . . ) or a thin film approach (e.g., by sputtering, thermal spraying, and/or cold spraying conductive material). Coplanar conductors 8 may be partitioned using, for example, laser ablation such that they are electrically isolated from one another. It should be understood that the configuration of conductors 8 in the Figures described here are merely for illustrative purposes only and a person of ordinary skill in the art will appreciate that conductors 8 may be distributed on planar substrate 2 in a variety of alternative ways.

The dielectric layer 10 may be comprised of one or more individual layers that are collectively referred to as the dielectric layer 10. The one or more planar dielectric layers 10 have a bottom surface 12 disposed adjacent to the upper surface 4 of the planar substrate 2—the coplanar conductors 8 being sandwiched there between—and an upper surface 14 disposed a distance from the bottom surface 12 along the transverse direction T. The coplanar conductors 8 may be formed using a variety of methods and materials known to a person of ordinary skill in the art. For example, coplanar conductors 8 may be made by laminating a dielectric onto the planar substrate using an adhesive layer (or another means of adhesion) disposed in between the dielectric layer 10 and the planar substrate 2. Alternatively, the coplanar conductors 8 themselves could be formed using a pressure sensitive adhesive layer or can be integrated into planar substrate 2 by forming dielectric layer(s) 10 directly on top of upper surface 4 and coplanar conductors 8. The dielectric layer 10 may also be comprised of a DTE insulating layer (such as a thick film dielectric or polymer/non-conductive film).

The dielectric layer(s) 10 may also define a liquid flow path 16 integrated into the dielectric layer(s) 10 which defines a path liquid whole blood may flow through. An example of flow path 16 has two side walls 18 and a bottom surface 20 extending between the two side walls 18. The two side walls 18 extend along the longitudinal direction L and the transverse direction T—at least part of the distance from the upper surface 14 to the upper surface 4. In various embodiments, the flow path 16 may have a lid which at least partially encloses the flow path 16—although this configuration is now shown in FIG. 1A or 1B.

Sensor assembly 100 may also comprise wells 22. Wells 22 are holes (also known as apertures) in the dielectric layer 10 that are open to the flow path 16 and extend along the transverse direction T between an upper surface 14 of the dielectric layer 10 and the upper surface 4 of the planar substrate 2. If an adhesive layer is present, wells 22 may also extend through the adhesive layer disposed in between the dielectric layer 10 and the planar substrate 2. The cross section of respective wells 22 extend along the lateral direction A and the longitudinal direction L. The cross section of respective wells 22 may be circular, ovular, or any other regular or irregular shape. Individual wells 22 may be positioned over respective conductors 8 and may contain membrane chemistries 24 (also known as reagents) dispensed therein such that the membrane chemistries 24 contact the respective conductors 8 underneath. While the wells 22 in FIGS. 1A and 1B are depicted as being evenly spaced along line A-A' it should be understood that they can be arranged in a variety of alternative configurations. In the event assay device 100 does not have a flow path 16, the whole blood can flow along the upper surface 14 of the dielectric layer 10 and wells can extend to the upper surface 14 of the dielectric layers 10.

When the sample whole blood along the flow path 16 or along upper surface 14 of the dielectric layer 10, the sample whole blood comes into contact with the membrane chemistries 24 in each well 22. The membrane chemistries 24 in each respective well 22 then react with analytes of interest present in the whole blood sample—thereby inducing a detection signal within the associated conductor 8. The detection signal can then be interpreted in order to determine the intercellular concentration of the analyte of interest in the sample fluid. The combination of a well 22, membrane chemistries 24 contained therein, as well as the associated conductor 8 may be collectively referred to as an analyte sensor 30 (also referred to as an ion selective electrode (ISE)). Example membrane chemistries 24 may react with analytes and/or properties of the whole blood, such as, but not limited to, magnesium ions ($Mg^{2+}$), calcium ions ($Ca^{2+}$), and sodium ions ($Na^+$), potassium ions ($K^+$), lactate ion, glucose, pH, Bicarbonate ($HCO_3^-$), and chloride (Cl). It should be understood that an analyte sensor 30 may be referred to by the analyte the associated chemistry 24 reacts to. For example, an analyte sensor 30 with chemistry 24 reactive to $Mg^{2+}$ may be referred to as an $Mg^{2+}$ sensor.

As depicted in FIGS. 2A and 2B, a sensor assembly 200 bonded sensor assembly 100. FIG. 2A is a top view of sensor assembly 200 while FIG. 2B is a side view of sensor assembly 200 along line A-A'. As depicted in FIGS. 2A and 2B, sensor assembly 200 is substantially similar to sensor assembly 100 is disposed such that the reaction wells 22 of sensor assembly 100 face the wells of sensor assembly 200 opposite the flow path 18.

In an illustrative embodiment, sensor assembly 100 or sensor assembly 200 include a minimum of a first analyte sensor 32, a second analyte sensor 34, and a third analyte sensor 36. The first analyte sensor 32 and the second analyte sensor 34 each contain chemistry 24 that is reactive to a first analyte and a second analyte, respectively, within the plasma of whole blood. In whole blood, both the first analyte and the second analyte have a concentration within red blood cells (RBCs) (the concentration within RBCs being referred to as the intracellular concentration) that is higher than the concentration within the surrounding plasma (the concentration within the surrounding plasma being referred to as the intercellular concentration). Examples of analytes known to have an intracellular concentration higher than the intercellular concentration include, but are not limited to, potassium ions and magnesium ions. For example, a normal intracellular concentration of both potassium ions is above 20-40 times higher than a normal intercellular concentration of potassium ions.

The third analyte sensor 36 contains chemistry 24 that is reactive to a third analyte in the plasma of whole blood. The third analyte has an intracellular concentration within RBCs that is lower than the intercellular concentration within the surrounding plasma. Examples of third analytes known to have an intracellular concentration lower than the intercellular concentration include, but are not limited to, calcium ions and sodium ions. For example, a normal intracellular concentration of sodium ions is about 8-12 times lower than a normal intercellular concentration of sodium ion.

In additional embodiments of the invention, one or more additional sensors which function like the first, second, or third analyte sensors may also be utilized.

When individual RBCs rupture, their intracellular components mix with the whole blood plasma. As a whole blood sample become increasingly hemolyzed and an increasingly large number of RBCs rupture, the intracellular components of the ruptured RBCs—like the first, second, and third analytes contained therein—will mix in with the plasma and impact the concentration of those same analytes within the plasma. For example, the relatively high intracellular concentration of the first analyte and the second analyte released from ruptured RBCs will increase the otherwise relatively low intercellular concentration of the first analyte and the second analyte. Thus, the extent to which the intercellular concentration of the first and second analyte in plasma exceeds a normal value is an indication of the extent of hemolysis in the whole blood sample. As should be understood by those skilled in the art, the change in intercellular concentration due to hemolysis will be the more pronounced the higher the intracellular concentration of an analyte is as compared to the intercellular concentration in non-hemolyzed whole blood.

In contrast, analytes with an intracellular concentration lower than their intercellular concentrations will have the reverse impact. The relatively low intracellular concentration of the third analyte released from ruptured RBCs will begin to decrease (i.e., dilute) the otherwise relatively high intercellular concentration of the third analyte. Thus, an intercellular concentration of the third analyte below a normal value may be used as another indicator of the degree of hemolysis in the whole blood sample. As should be understood by those skilled in the art, this dilution effect will be the more pronounced the lower the intracellular concentration of the third analyte is as compared to the intercellular concentration in non-hemolyzed whole blood.

In an illustrative embodiment, sensor assembly 100 or sensor assembly 200 may also include a fourth analyte sensor 38. The fourth analyte sensor 38 contains chemistry that is reactive to a fourth analyte in the plasma of the whole blood. The fourth analyte has an intercellular concentration that decreases as hemolysis increases (e.g., the intracellular concentration is lower than the intercellular concentration). Further, the fourth analyte may not be present within the RBCs of the whole blood sample (and therefore does not have an intracellular concentration). An example of a fourth analyte is lactate. Lactate, while present in plasma is not present within RBCs. As RBCs rupture, however, they release lactate enzymes which consume, via an enzymatic reaction, lactate—thereby lowering the concentration of lactate within the plasma.

The detection signals associated with one or more of the first analyte sensor 32, the second analyte sensor 34, the third analyte sensor 36, and the fourth analyte sensor 38 can therefore be used to determine not only the intercellular concentration of the first, second and third analytes, but the whole blood sample's degree of hemolysis as well—thereby avoiding the need for sensor with a depicted hemolysis sensor and/or separate testing equipment.

An exemplary method of determining the degree of hemolysis using the first, second and third analytes will now be described with reference to process 300, as depicted in FIG. 3. It should be understood that, while the blocks of FIG. 3 are shown in an exemplary order, the actions described there can be performed in a variety of different orders. Thus the order the blocks are placed in FIG. 3 is a non-limiting example.

In block 305, the intercellular concentration of the first analyte is determined. This determination can be made by interpreting the detection signal in the conductor 8 of the first analyte sensor 32. This determination can be made by a processor located within the same deceive as sensor assembly 100 or in a separate, external device. Similarly, the intercellular concentrations of the second analyte and the third analyte are determined are determined in blocks 310 and 315, respectively.

In block 320, a first ratio of the first intercellular analyte concentration to the third intercellular analyte concentration in the whole blood is determined. The first ratio can be expressed as the relationship of the first intercellular analyte concentration to the second intercellular analyte and can be written as, for example: '(first intercellular analyte concentration):(third intercellular analyte concentration)" or vice versa. The first ratio can also be converted to a fraction by dividing the first intercellular analyte concentration by the third intercellular analyte concentration or vice versa. Similarly, in block 325, a second ratio of the second intercellular analyte concentration to the third intercellular analyte concentration in the whole blood is computed. In an alternative embodiment of FIG. 3, the performance of block 325 is optional and hemolysis detection is made using the first ratio by itself. However, it should also be appreciated that hemolysis can be more accurately determined by factoring in more than one analyte concentrations.

In block 330, of the level of hemolyzation in the whole blood sample is determined based on the first ratio and, if available, the second ratio. This determination can be established, in part, by comparing the first ratio to a first reference ratio (or set of first reference ratios) and by comparing of the computed second ratio to a second reference ratio (or set of second reference ratios). The first reference ratio and the second reference ratio may be computed based on average intercellular concentrations of the first analyte, the second analyte, and the third analyte found in average samples of whole blood. For example, assuming the average intercellular values of the first analyte, the second analyte, and the third analyte are 0.5 mM, 0.5 mM, and 1.2 mM, respectively, both the first reference ratio and the second reference ratio can be expressed as 0.5:1.2 (i.e., as a relationship) or 0.416 (i.e., as a fraction where the concentration of the third analyte is used as the denominator when computing the ratio).

The extent by which the first ratio and—if block 325 was performed—the second ratio differs from the respective first and second reference ratios can be correlated to the level of hemolysis. For example, if neither the first ratio nor the second ratio sufficiently differs from the respective first and second reference ratio(s), the sample is determined to not have an elevated level of hemolysis. However, if one, but not both, of the first ratio and the second ratio differ sufficiently from the respective first and second reference ratio(s), the associated whole blood can be determined to have an approximately normal level of hemolysis. This may be caused where a medical condition—and not hemolysis—results in elevated levels of one, but not both of the first analyte and the second analyte. In an alternative embodiment, if one, but not both, of the first ratio and the second ratios differ sufficiently from the respective first and second reference ratio(s), the associated whole blood sample can be flagged for additional testing to determine the extent of hemolyzation.

The determination of block 330 also factors in whether one or both of the first intercellular concentration and the second intercellular concentration exceed a respective threshold concentration. Each respective threshold concentration can be an established normal concentration value of the respective first analyte and the second analyte in typical whole blood sample or a concentration slightly above the established value(s) (for example, 3%, 5%, 7%, 10%, 12%, 15%, 17% or 20% higher than the established normal concentration). If both the first intercellular concentration and the second intercellular concentration exceed their respective threshold concentrations, then the first and second intercellular ratios can be used to quantify the extent of the hemolyzation above normal levels. If, however, one or both of the first intercellular concentration or the second intercellular concentration do not exceed their respective threshold concentrations, the whole blood sample can either be determined to not have elevated levels of hemolysis or be flagged for additional testing.

It should be appreciated that the first ratio and the second ratio are particularly sensitive to the hemolysis level because they are a ratio of an analyte concentration that increases with the level of hemolysis (i.e., the first analyte and the second analyte concentrations) and an analyte concentration that decreases with the level of hemolysis (i.e., the third analyte concentration). Thus, the resulting first and second ratios accentuate the effects of hemolysis—making it easier to detect and quantify the degree of hemolysis. For example, assume an illustrative sample of whole blood is sufficiently hemolyzed to (1) increase each of the first and second intercellular analyte concentrations from an average value of 0.5 mM to 0.6 mM and 0.56 mM, respectively, and (2) decrease the third intercellular analyte concentration from an average value of 1.2 mM to 1.15 mM—resulting in a first and second ratio of 0.521 and 0.487, respectively. When viewed by themselves, the first, second, and third intercellular analyte concentrations may not definitively indicate the illustrative sample is hemolyzed. However, the level of hemolysis is more pronounced when comparing the first ratio of 0.521 to the first reference ratio of 0.416 and the second ratio of 0.487 to the second reference ratio of 0.416.

In block 335, the results of the determination are reported to a healthcare provider. Examples of this reporting include, but are not limited to, a print out, an electronic communication, a visual alert, and/or an audio alert.

FIG. 3 also contains optional block 340. In optional block 340, a fourth concentration of the fourth analyte is computed. The fourth concentration of the fourth analyte can be computed using the detection signal of the conductor 8 associated with the fourth analyte sensor 38. The fourth analyte has an intercellular concentration that decreases with the level of hemolysis due primarily to an enzymatic reaction. Further, the fourth analyte may not be present within the RBCs of the whole blood sample (and therefore does not have an intracellular concentration). An example of a fourth analyte is lactate. When hemolysis occurs, lactate enzymes from within the ruptured RBCs mix with the surrounding plasma and consume the lactate in the plasma. This enzymatic reaction causes the concentration of lactate within the plasma to decline. It should be appreciated that the concentration of lactate will decline, to some extent, due to the dilution of the plasma with the contents of ruptured RBCs. However, the above enzymatic reaction can largely be attributed with the decline of lactate below an average value(s) within a whole blood sample. Thus the extent of the decline in lactate in the plasma can be largely attributed to the extent of the hemolysis within the sample. When desired, the concentration of the fourth analyte can be factored into the determination in block 330.

It should also be appreciated that hemolysis can be more accurately determined by factoring in multiple analyte concentrations. Thus, in alternative embodiment of FIG. 3, the concentration from one or more additional sensors which function like the first, second, or third analyte sensors may also be utilized. These additional sensors may provide concentration information that can be used to determine additional ratios similar to the first ratio, the second ratio, or the third ratio.

Figure 4:
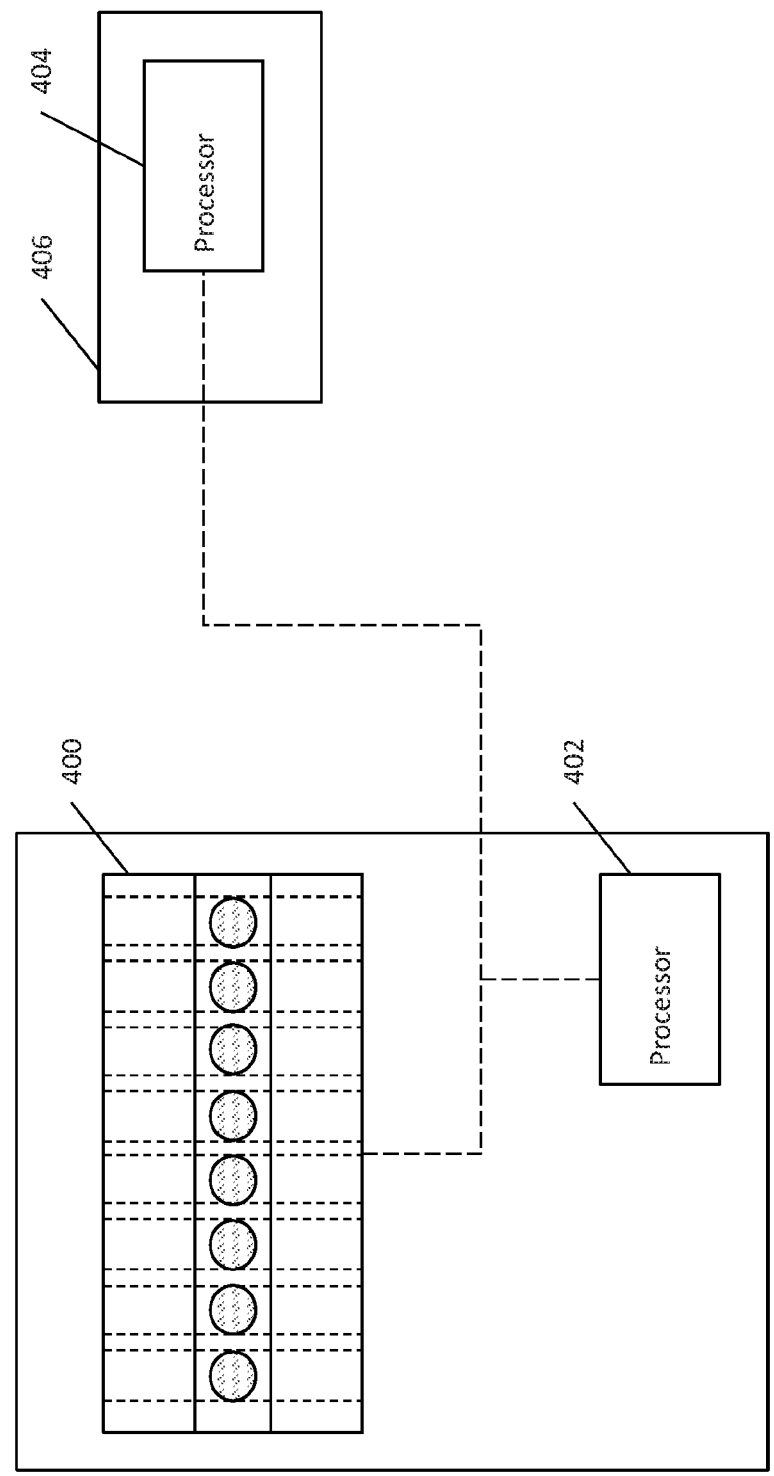
FIG. 4 depicts a device for interfacing with a sensor assembly.

FIG. 4 depicts a device 400, such as one or both of sensor assemblies 100 and 200, for interfacing with one or both of sensor assemblies 100 and 200. For example, the electrical contacts described above enable the device 400 to be electrically connected to an internal processor 402. Alternatively, or in addition to, an internal processor 402, diagnostic device 400 may be electrically coupled to a remote processor 404 disposed in a separate device 406.

Processors 402 and 404 may have any suitable architecture, such as a general processor, central processing unit, digital signal processor, application specific integrated circuit, field programmable gate array, digital circuit, analog circuit, combinations thereof, or any other now known or later developed device for processing data. Likewise, processing strategies may include multiprocessing, multitasking, parallel processing, and the like. A program may be uploaded to, and executed by, the processor. The processor implements the program alone or includes multiple processors in a network or system for parallel or sequential processing.

The processor may perform the workflows, machine learning, model training, model application, and/or other processes described herein. For example, the processor or a different processor is operable perform the steps shown and described in connection with FIG. 3.

The processor outputs the state and/or associated information on the display, into a memory, over a network, to a printer, or in another media. The display is text, graphical, or other display.

The display is a CRT, LCD, plasma, projector, monitor, printer, or other output device for showing data. The display is operable to output to a user a state associated with a patient. The state provides an indication of whether a medical concept is indicated in the medical transcript. The state may be whether a disease, condition, symptom, or test result is indicated. In one embodiment, the state is limited to true and false, or true, false and unknown. In other embodiments, the state may be a level of a range of levels or other non-Boolean state.

The processor operates pursuant to instructions. The instructions and/or patient records for training a probabilistic model or for inferring a medical concept from a medical transcript are stored in a computer readable memory such as an external storage, ROM, and/or RAM. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system. Because some of the constituent system components and method acts depicted in the accompanying figures may be implemented in software, the actual connections between the system components (or the process steps) may differ depending upon the manner of programming.

The following is a non-limiting list of illustrative embodiments:

1. A system comprising at least one processor and a non-transitory computer-readable medium that stores instructions that, when executed by the at least on processor cause the system to determine a level of hemolysis of a sample of whole blood, by: receiving a first intercellular concentration of a first compound in the whole blood sample, the first intercellular concentration having been obtained from a first sensor disposed on a sensor cartridge, the first sensor being specific to the first compound, an intracellular concentration of the first compound being higher than the intercellular concentration in the whole blood sample; receiving a second intercellular concentration of a second compound in the whole blood sample, the second concentration having been obtained from a second sensor on the sensor cartridge that is specific to the second compound, an intracellular concentration of the second compound being higher than the intercellular in the whole blood sample; receiving a third intercellular concentration of a third analyte, the third concentration having been obtained from a third sensor on the sensor cartridge that is specific to the third compound, the third analyte being a compound with an intracellular concentration lower than the intercellular concentration in the whole blood sample; computing a first ratio of the first concentration to the third concentration; computing a second ratio of the second concentration to the third concentration, and determining the degree of hemolyzation of the whole blood sample based on the first ratio and the second ratio; and outputting the determination to a medical professional.

2. The system of illustrative embodiment 1, wherein the first compound is potassium ions ('K+'), and the first concentration is obtained from a K+ ion selective electrode on the sensor cartridge; wherein the second compound is magnesium ions (Mg++) and the second concentration is obtained from a Mg++ ion selective electrode on the sensor cartridge; and wherein the third compound is sodium ions (Na++) or calcium ions (Ca++) and the third concentration is obtained from corresponding Na++ or Ca++ ion selective electrode on the sensor cartridge.

3. The system of any of illustrative embodiments 1 or 2, further comprising the steps of: receiving a fourth intercellular concentration of a fourth compound in the whole blood sample, the fourth concentration having been obtained from a fourth sensor on the sensor cartridge that is specific to the fourth compound, the fourth intercellular concentration of the fourth compound having an inverse relationship with the amount of hemolysis in the whole blood; determining the degree of hemolyzation based on the first ratio, the second ratio, the third concentration, and the fourth intercellular concentration; and outputting the determination to a medical professional.

4. The system of illustrative embodiment 3, wherein the fourth compound is lactates the fourth intercellular concentration is obtained from a lactate ion selective electrode on the sensor cartridge.

5. The system of any of illustrative embodiments 1 to 4, wherein the step of outputting further comprises outputting the first concentration, the second concentration, and the third concentration.

6. The system of any of illustrative embodiments 1 to 5, wherein the first wherein the first intercellular concentration is above a first reference intercellular concentration, and wherein the second intercellular concentration is above a second reference intercellular concentration.

7. A system comprising at least one processor and a non-transitory computer-readable medium that stores instructions that, when executed by the at least on processor cause the system to determine a level of hemolysis of a sample of whole blood, by: administering whole blood to a sensor cartridge containing at least a K, Mg, Ca, and lactate sensor; determining a first intercellular concentration of a first compound in the whole blood sample, the first concentration having been obtained from a first sensor disposed on a sensor cartridge, the first sensor being specific to the first compound, an intracellular concentration of the first compound being higher than the intercellular concentration in the whole blood sample; determining a second intercellular concentration of a second compound in the whole blood sample, the second concentration having been obtained from a second sensor on the sensor cartridge that is specific to the second compound, an intracellular concentration of the second compound being higher than the intercellular in the whole blood sample; determining a third intercellular concentration of a third analyte, the third concentration having been obtained from a third sensor on the sensor cartridge that is specific to the third compound, the third analyte being a compound with an intracellular concentration lower than the intercellular concentration in the whole blood sample; computing a first ratio of the first concentration to the third concentration; computing a second ratio of the second concentration to the third concentration; determining the degree of hemolyzation of the whole blood sample based on the first ratio and the second ratio; and outputting the determination to a medical professional.

8. The system of illustrative embodiment 7, wherein the first compound is potassium ions (K+), and the first concentration is obtained from a K+ ion selective electrode on the sensor cartridge; wherein the second compound is magnesium ions (Mg++) and the second concentration is obtained from a Mg++ ion selective electrode on the sensor cartridge; and wherein the third compound is sodium ions (Na++) or calcium ions (Ca++) and the third concentration is obtained from corresponding Na++ or Ca++ ion selective electrode on the sensor cartridge.

9. The system of any of illustrative embodiments 7 or 8, further comprising the steps of: determining a fourth intercellular concentration of a fourth compound (lactate) in the whole blood sample, the fourth concentration having been obtained from a fourth sensor on the sensor cartridge that is specific to the fourth compound, the fourth intercellular concentration of the fourth compound having an inverse relationship with the amount of hemolysis in the whole blood; determining the degree of hemolyzation based on the first ratio, the second ratio, the third concentration, and the fourth intercellular concentration; and outputting the determination to a medical professional.

10. The system of illustrative embodiment 9, wherein the fourth compound is lactates the fourth intercellular concentration is obtained from a lactate ion selective electrode on the sensor cartridge.

11. The system of any of illustrative embodiments 7 to 10, wherein the step of outputting further comprises outputting the first concentration, the second concentration, and the third concentration.

12. The system of any of illustrative embodiments 7 to 11, wherein the first wherein the first intercellular concentration is above a first reference intercellular concentration, and wherein the second intercellular concentration is above a second reference intercellular concentration.

What is claimed is:

1. A system comprising at least one processor and a non-transitory computer-readable medium that stores instructions that, when executed by the at least one processor, cause the system to determine a level of hemolysis of a sample of whole blood, by:
  receiving a first intercellular concentration of a first ion in the whole blood sample, the first intercellular concentration having been obtained from a first ion selective electrode disposed on a sensor cartridge, the first ion selective electrode being specific to the first ion, an intracellular concentration of the first ion being higher than the intercellular concentration in the whole blood sample;
  receiving a second intercellular concentration of a second ion in the whole blood sample, the second intercellular concentration having been obtained from a second ion selective electrode on the sensor cartridge that is specific to the second ion, an intracellular concentration of the second ion being higher than the intercellular in the whole blood sample;

receiving a third intercellular concentration of a third ion, the third intercellular concentration having been obtained from a third ion selective electrode on the sensor cartridge that is specific to the third ion, the third ion having an intracellular concentration lower than the intercellular concentration in the whole blood sample, and the first, second, and third ions being different from one another;

computing a first ratio of the first intercellular concentration to the third intercellular concentration;

computing a second ratio of the second intercellular concentration to the third intercellular concentration, and determining the degree of hemolyzation of the whole blood sample based on the first ratio and the second ratio; and outputting the determination to a medical professional.

2. The system of claim 1, wherein:

the first ion is potassium ions ('$K^+$'), and the first intercellular concentration is obtained from a $K^+$ ion selective electrode on the sensor cartridge;

the second ion is magnesium ions (Mg++), and the second intercellular concentration is obtained from a Mg++ ion selective electrode on the sensor cartridge; and the third ion is sodium ions (Na++) or calcium ions (Ca++), and the third intercellular concentration is obtained from corresponding Na++ or Ca++ ion selective electrode on the sensor cartridge.

3. The system of claim 1, further comprising the steps of:

receiving a fourth intercellular concentration of a fourth ion in the whole blood sample, wherein the fourth ion is different from the first, second, and third ions, the fourth intercellular concentration having been obtained from a fourth ion selective electrode on the sensor cartridge that is specific to the fourth ion, the fourth intercellular concentration of the fourth ion having an inverse relationship with the amount of hemolysis in the whole blood;

determining the degree of hemolyzation based on the first ratio, the second ratio, the third intercellular concentration, and the fourth intercellular concentration; and outputting the determination to a medical professional.

4. The system of claim 3, wherein the fourth ion is lactate ion, and the fourth intercellular concentration is obtained from a lactate ion selective electrode on the sensor cartridge.

5. The system of claim 1, wherein the step of outputting further comprises outputting the first intercellular concentration, the second intercellular concentration, and the third intercellular concentration.

6. The system of claim 1, wherein the first intercellular concentration is above a first reference intercellular concentration, and wherein the second intercellular concentration is above a second reference intercellular concentration.

7. A system comprising at least one processor and a non-transitory computer-readable medium that stores instructions that, when executed by the at least one processor, cause the system to determine a level of hemolysis of a sample of whole blood, by:

administering whole blood to a sensor cartridge containing at least a potassium ion selective electrode, a magnesium ion selective electrode, a lactate ion selective electrode, and one of a calcium or sodium ion selective electrode;

determining a first intercellular concentration of a first ion in the whole blood sample, the first intercellular concentration having been obtained from one of the ion selective electrodes disposed on a sensor cartridge, an intracellular concentration of the first ion being higher than the intercellular concentration in the whole blood sample;

determining a second intercellular concentration of a second ion in the whole blood sample, the second intercellular concentration having been obtained from a second of the ion selective electrodes disposed on the sensor cartridge, an intracellular concentration of the second ion being higher than the intercellular in the whole blood sample;

determining a third intercellular concentration of a third ion, the third intercellular concentration having been obtained from a third of the ion selective electrodes disposed on the sensor cartridge, the third ion having an intracellular concentration lower than the intercellular concentration in the whole blood sample;

computing a first ratio of the first intercellular concentration to the third intercellular concentration;

computing a second ratio of the second intercellular concentration to the third intercellular concentration;

determining the degree of hemolyzation of the whole blood sample based on the first ratio and the second ratio; and outputting the determination to a medical professional.

8. The system of claim 7, wherein:

the first ion is potassium ions ('$K^+$'), and the first intercellular concentration is obtained from the $K^+$ ion selective electrode on the sensor cartridge;

the second ion is magnesium ions (Mg++), and the second intercellular concentration is obtained from the Mg++ ion selective electrode on the sensor cartridge; and the third ion is sodium ions (Na++) or calcium ions (Ca++), and the third intercellular concentration is obtained from the corresponding Na++ or Ca++ ion selective electrode on the sensor cartridge.

9. The system of claim 7, further comprising the steps of:

determining a fourth intercellular concentration of a fourth ion in the whole blood sample, the fourth intercellular concentration having been obtained from a fourth of the ion selective electrodes disposed on the sensor cartridge, the fourth intercellular concentration of the fourth ion having an inverse relationship with the amount of hemolysis in the whole blood;

determining the degree of hemolyzation based on the first ratio, the second ratio, the third intercellular concentration, and the fourth intercellular concentration; and outputting the determination to a medical professional.

10. The system of claim 9, wherein the fourth ion is lactate ion, and wherein the fourth intercellular concentration is obtained from the lactate ion selective electrode on the sensor cartridge.

11. The system of claim 7, wherein the step of outputting further comprises outputting the first intercellular concentration, the second intercellular concentration, and the third intercellular concentration.

12. The system of claim 7, wherein the first intercellular concentration is above a first reference intercellular concentration, and wherein the second intercellular concentration is above a second reference intercellular concentration.

* * * * *